United States Patent [19]

Della Croce

[11] 4,273,533
[45] Jun. 16, 1981

[54] METHOD FOR CONSTRUCTING DENTURES

[76] Inventor: John B. Della Croce, 450 Washington St., Freeland, Pa. 18224

[21] Appl. No.: 65,484

[22] Filed: Aug. 10, 1979

[51] Int. Cl.³ .............................................. A61C 11/00
[52] U.S. Cl. ...................................... 433/55; 433/71; 433/213
[58] Field of Search .......................... 433/55, 71, 213

[56] References Cited

U.S. PATENT DOCUMENTS 2,754,589  7/1956  Highkin .................................. 433/55

Primary Examiner—Robert Peshock
Attorney, Agent, or Firm—Steele, Gould & Fried

[57] ABSTRACT

In the construction of dentures, a method for calibrating an articulator, comprising the steps of forming a set of intra oral gothic arch traces, the traces defining a three dimensional envelope of motion, and utilizing the intra oral traces to form a substantially identical second set of gothic arch traces on the articulator, whereby relative movement of the articulator may be confined to the envelope of motion.

12 Claims, 5 Drawing Figures

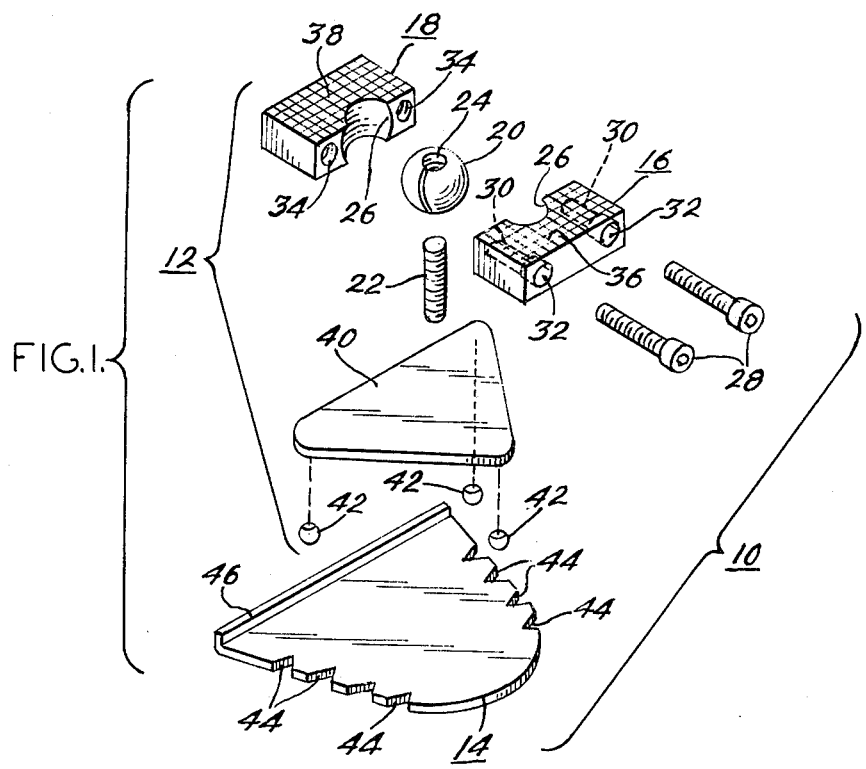
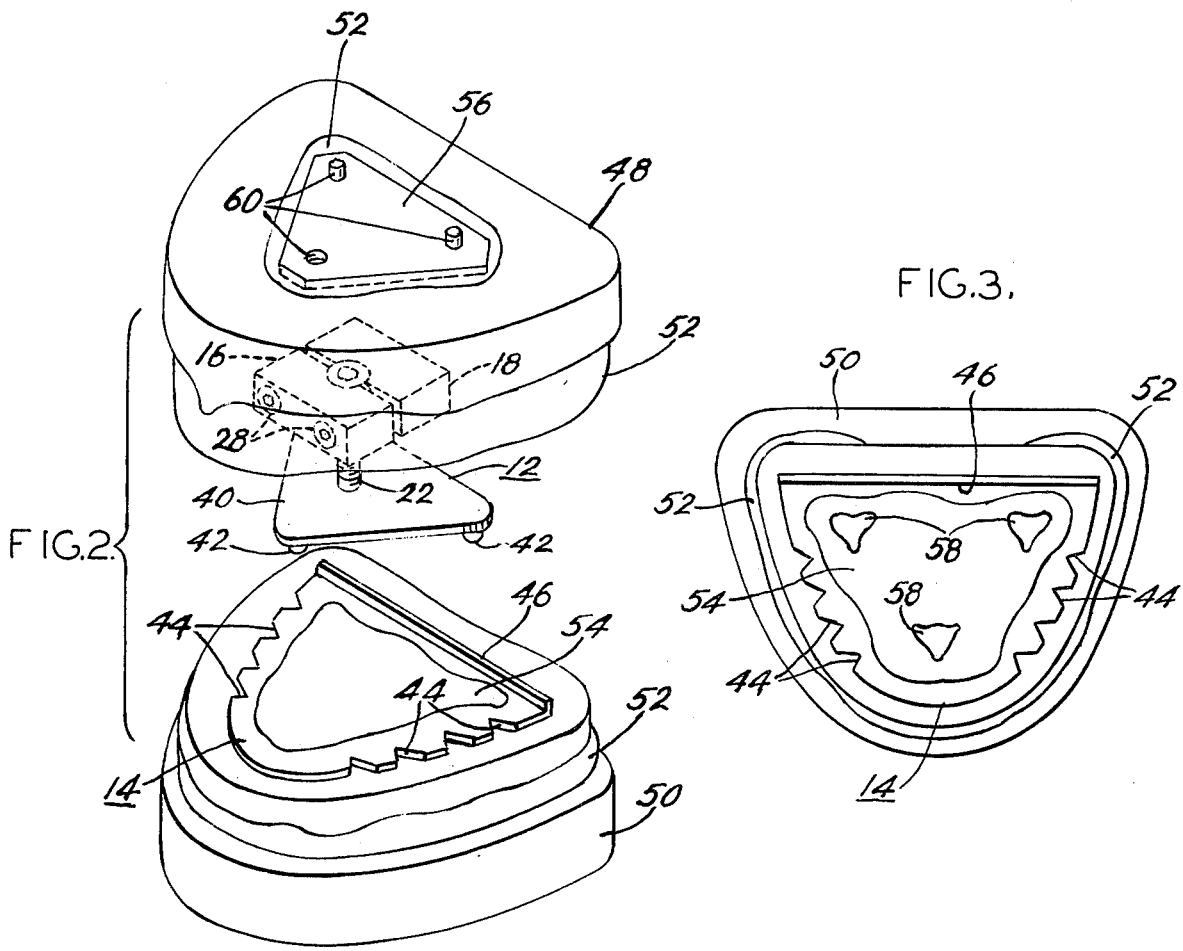

METHOD FOR CONSTRUCTING DENTURES

BACKGROUND OF THE INVENTION

1. Field of the Invention

This invention relates in general to the field of dentistry, and in particular, to a novel method and novel apparatus for constructing dentures.

2. Prior Art

In the construction of dentures, one of the most significant problems is to orient the upper and lower casts, in which the artificial teeth are set, relative to one another, in such a manner that the movements of the mandible and its neuro-muscular influences will be modeled in a true and reproducible form. Such movements, or registrations, must not only be reproducible, but definite and durable as well. Further, once such registrations are made, it must be possible to transfer the registrations to an instrument such as an articulator, without introducing any error, in order to actually construct a dentition that will be in agreement with the original registrations of jaw movement.

The human jaw is capable of the widest variety of movements. Modelling such movements is complicated by the fact that the lower jaw is not merely connected by a hinge, and is capable of translational movement as well. Accordingly, when seeking to model or reproduce such movement, one must be concerned with rotary or hinge-like motion, which depends upon the centers of rotation of the condoyles with respect to the glenoid fossa, as well as translational motion, which results from motion of the condoyle along the articular eminence. Other movements result from the combination of rotary and translational motion, as well as from bodily (mandibular) motion, or Bennett movement. To further complicate matters, all of the foregoing are controlled to some extent by biological factors in the formation of ligaments, meniscus and musculature, emotional factors and habit patterns, as well as the shape of the bony structures, including condoyle, articular eminence, articular fossa and incisal guidance, if present. Incisal guidance is not present as such in totally edentulous mouths.

All of the foregoing factors contribute to the definition of a three dimensional envelope of motion, which defines or describes all of the natural movements of the jaw for any particular person.

Intra oral tracing apparatus are known which utilize moldable material and scribing pins for forming what are called gothic arch traces. A set of at least three such gothic arch traces, made in accordance with relative movements of the human jaw, accurately define the three dimensional envelope of motion described above. Although some such apparatus are known, their accuracy has been to limited avail, because no articulators are known in the art which can utilize such gothic arch traces in a manner which precisely models or reproduces the three dimensional envelope of motion unique to each individual.

This deficiency in the prior art is due to an unjustified belief that the solution lies in the development of a so-called universal articulator, which is capable of reproducing each and every movement of each and every jaw. The prior art is replete with such articulators, each of which utilizes some form of hinged or pivotal connection in order to simulate movement between upper and lower dentures, and therefore upper and lower jaws.

In a distinct departure from this prior art, this invention teaches the elimination of the so called universal articulator, and instead, teaches a means by which an articulator may be programmed or calibrated to suit each individual patient, the method and apparatus being not only as accurate as humanly possible, but being quick and inexpensive as well. In the construction of dentures, a method for calibrating an articulator, according to this invention, comprises the steps of forming a set of intra oral gothic arch traces, the traces defining a three dimensional envelope of motion, and utilizing the intra oral traces to form a substantially identical set of gothic arch traces on the articulator, whereby relative movement of the articulator may be confined to the envelope of motion. An articulator according to this invention for constructing dentures, for use with a gothic arch tracing apparatus, comprises first and second members, having means for holding the members in spaced relationship, without being connected, and having means for mounting dental casts between the members, said casts having tracing apparatus disposed therein, in operable relationship, and means for forming a set of gothic arch traces, for controlling relative movement of the members, in accordance with movement of the tracing apparatus.

Only one unhinged articulator is known in the art, however, it too seeks to be a universal articulator, by reason of its reliance on removable analog blocks to define movement of the articulator. Further, this articulator has upper and lower frames, each of which has a defined horizontal axis of rotation and a centric reference device for centering the upper frame laterally with reference to the lower frame. Such predefined axes and references introduce errors into the modelling process before it has even begun. By way of contrast, the method and apparatus taught herein make no such predefinitions, and are therefore significantly more accurate.

SUMMARY OF THE INVENTION

It is an object of this invention to provide an improved method for constructing dentures.

It is another object of this invention to provide improved apparatus for constructing dentures, including intra oral tracing apparatus and articulator.

It is a further object of this invention to provide method and apparatus for constructing dentures wherein movements of the jaw may be recorded and substantially identically reproduced.

It is yet another object of this invention to provide method and apparatus for constructing dentures wherein the articulator can be calibrated to precisely model the envelope of motion which uniquely describes the movement of each individual jaw, rather than utilizing the nearest approximation of a universal articulator.

It is yet another object of this invention to provide method and apparatus for constructing dentures wherein intra oral gothic arch traces may be reproduced in an unhinged articulator.

These and other objects of this invention are accomplished by the method for calibrating an articulator, comprising the steps of forming a set of intra oral gothic arch traces, the traces defining a three dimensional envelope of motion, and utilizing the intra oral traces to form an identical second set of gothic arch traces on the articulator, whereby relative movement of the articulator may be confined to the envelope of motion.

In connection with this method, there is provided an intra oral tracing apparatus, comprising a tracing member and a scribing member, each of the members having means for removably mounting the member in a patient's mouth, and one of the members having universal adjustment means, the adjustment means being provided with locking means accessible through the patient's mouth.

In connection with this method an articulator is also provided, for use with gothic arch tracing apparatus, comprising first and second members, having means for holding the members in spaced relationship, without being connected, and having means for mounting dental casts between the members, said casts having said tracing apparatus disposed therein, in operable relationship, and means for forming a set of gothic arch traces, for controlling relative movement of the members in accordance with movement of the tracing apparatus.

Taken together, the method and apparatus provide a novel and highly accurate system for constructing dentures.

BRIEF DESCRIPTION OF THE DRAWINGS

For the purpose of illustrating this invention, there are shown in the drawings forms which are presently preferred, it being understood, however, that this invention is not limited to the precise arrangements and instrumentality shown.

FIG. 1 is an exploded perspective view of an intra oral tracing apparatus in accordance with this invention;

FIG. 2 is a perspective view, in diagramatic form, of the intra-oral tracing apparatus of FIG. 1 as mounted to upper and lower casts;

FIG. 3 is a top view of a typical set of gothic arch traces;

DETAILED DESCRIPTION OF THE PREFERRED EMBODIMENTS

Figure 4:
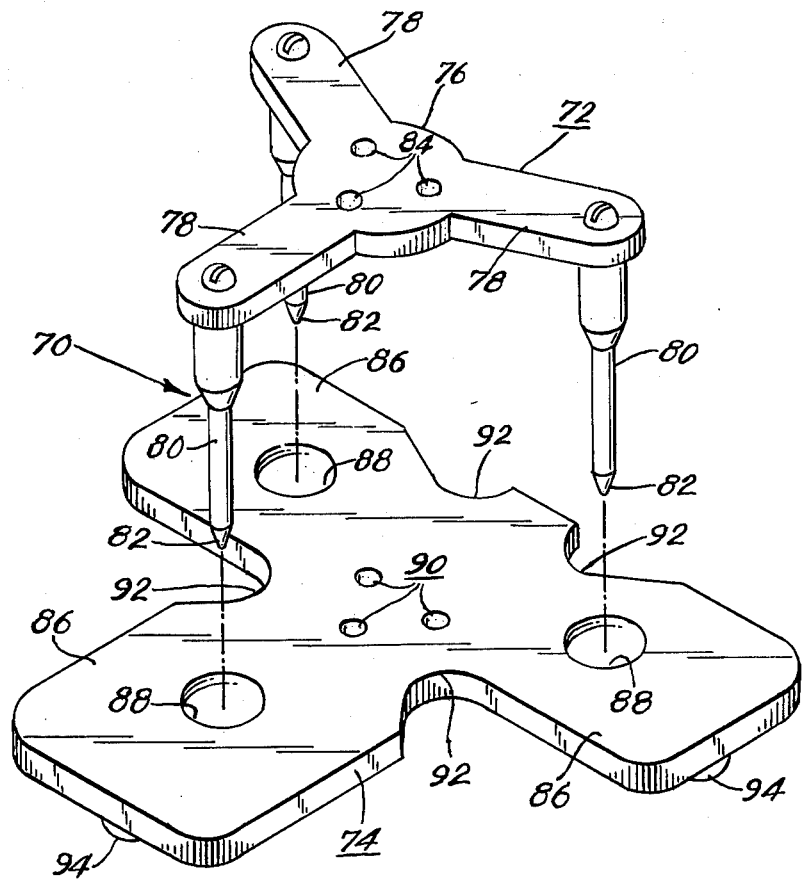
FIG. 4 is a perspective view of an articulator in accordance with this invention.

An intra oral gothic arch tracing apparatus according to this invention is shown in FIG. 1. The tracing apparatus 10 comprises a tracing member 12 and a tracing table 14.

The tracing member 12 comprises universal adjustment means, including front and rear block members 16 and 18, split ball 20 and threaded member 22. Threaded member 22 is insertable in threaded bore 24, in order to provide for verticle adjustment of the tracing member 12 with respect to the tracing table 14. Split ball 20 is rotatably and pivotally mounted within corresponding hemispherical grooves 26 in front and rear blocks 16 and 18. This provides for angular adjustment of the tracing member 12 with respect to the tracing table 14. Split ball 20 and threaded member 22 may be locked into position by lock screws 28, which fit through bores 30, each of which is provided with a counter bore 32 within which the heads of screws 28 will be disposed. The locking screws 28 are attached to rear block 18 by means of threaded bores 34, the heads of screws 34 exerting pressure against the walls of counter bores 32. Locking screws 28 may be provided with hex heads, in order to facilitate locking the member into position after it has been inserted into a patient's mouth. The upper surfaces 36 and 38 of front and rear blocks 16 and 18 respectively are provided with scores or depressions, in order to facilitate mounting the entire tracing member 12 as will be hereinafter described in more detail. A substantially equilateral triangular member 40 is fixedly secured to the bottom of threaded member 22, at right angles thereto. Members 22 and 40 may be adhesively bonded, soldered, spot welded, screwed or bolted together. Threaded member 22 may also be the shank portion of a bolt which is mounted through a hole in triangular member 40 from below, and secured thereto by any of the methods just described. Many means are available. Mounted near each corner of triangular member 40 is a stylus member 42, having a rounded point. Each stylus 42 may be attached in a manner similar to that described in connection with mounting triangular member 40 to threaded member 22. As a further alternative, each stylus 42 may be provided with a threaded base section, which can be screwed directly into a threaded bore in triangular member 40. At least three stylii 42 are necessary, but more may be used if desired.

Tracing table 14 is a substantially flat member, having a semicircular or rounded triangular configuration, which conforms generally to the curvature of the lower jaw. Tracing table 14 is provided with a plurality of notches 44 which aid in securing the tracing table as will be hereinafter described. Tracing table 14 may also be provided with a raised lip 46 along its straight edge.

FIG. 2 illustrates the tracing apparatus of FIG. 1 as it is attached in a patient's mouth. Although upper and lower dental forms or models 48 and 50, often termed casts, are illustrated, the mounting of the tracing apparatus is identical to that within a patient's mouth. During the course of constructing dentures, it is of course necessary in this method, as well as all other methods, to make upper and lower impressions of the patient's jaw. This is usually done with special modelling compounds or the like 52, which are pressed in and around the gums and existing teeth, for both the upper and lower jaw. The tracing member 12 and tracing table 14 are pressed into the modelling material 52 in the upper and lower jaws respectively, such that the tracing table 14 is substantially parallel to the lower jaw line, and the front and rear block assembly is substantially parallel to the upper jaw line.

Once the tracing member and tracing table have been embedded in the modeling material in the upper and lower jaws, the apparatus may be adjusted as follows. The patient is asked to hold his or her mouth open in a "natural" and comfortable position. Triangular member 40 may then be rotated, in order to increase or decrease the vertical distance between the triangular member 40 and the tracing table 14. After the vertical distance has been adjusted, to the natural position of the jaw for each individual patient, the triangular member 40, may or may not be parallel to tracing table 14. It is pivoted until it is substantially parallel, and then locking screws 28 are tightened, which may be conveniently accomplished by use of a hex, allen, ball or other suitable wrench inserted through the patient's opened mouth.

After the tracing apparatus has been adjusted, the patient is asked to open the mouth wide enough to enable the dentist or technician to cover the tracing table with a quick curing acrylic adhesive 54, or other moldable material. This can also be done outside the mouth before insertion of the tracing table into the mouth. The patient is then asked to open and close his or her mouth and to move the lower jaw in and out, back and forth, side to side, up and down and in any and all directions which feel natural, and which are not unduly exaggerated. During this motion, each stylus 42 will be displacing the acrylic material 54, forming a hole or groove therein. The motion of the jaws will take into account right and left lateral extremes, protrusive and retrusive movements and lateral protrusive right and left movements. These movements represent a three dimensional envelope of motion which is natural for any particular patient, and the grooves or traces formed in the moldable material are known as gothic arch traces. A set 58 of such traces is shown in FIG. 3. As shown, at least three such traces are necessary, although more may be made if desired.

After the moldable material has hardened or set, the upper and lower carrying trays, with the tracing apparatus still embedded, may be removed from the patient's mouth and inserted into the forms or casts 48 and 50, as shown in FIG. 2. The upper and lower casts may be provided with mounting means, such as substantially triangular plates 56, which are utilized to attach the casts to an articulator. These plates are embedded in modelling material 52 on the back of each cast. It may be emphasized that there has been obtained a set of gothic arch traces which define an envelope of motion unique to each individual patient.

Figure 5:
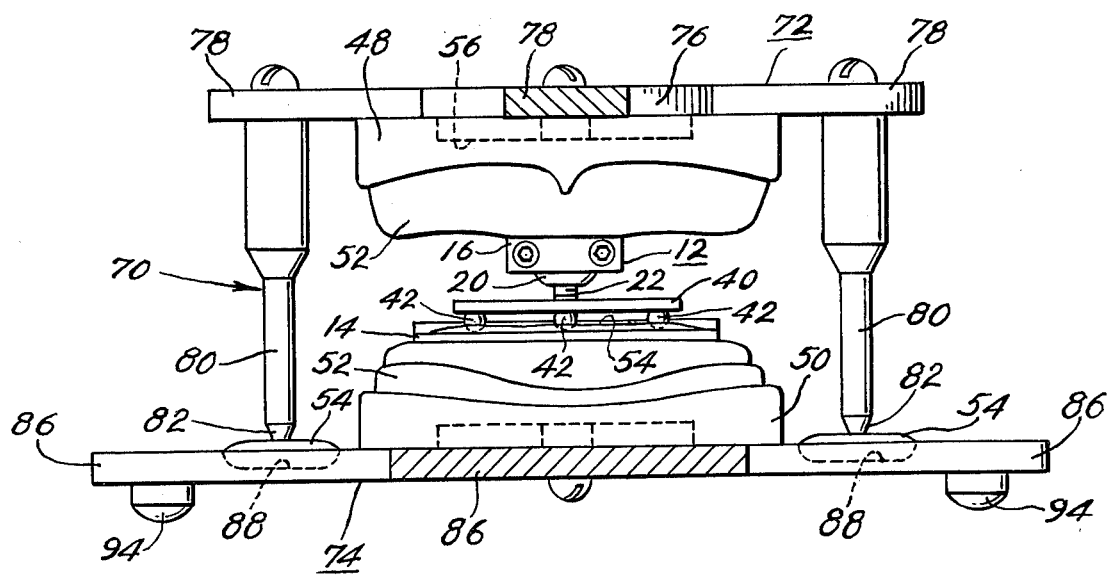
FIG. 5 is a front view of the articulator of FIG. 4, having the tracing apparatus of FIGS. 1 and 2 mounted thereto, in order to reproduce the gothic arch traces of FIG. 3 on the articulator, the front leg of the articulator having been omitted for clarity.

An articulator in accordance with this invention is shown in FIGS. 4 and 5. The articulator 70 comprises an upper member 72 and a lower member 74. Upper member 72 has a central portion 76, from which project three arms 78, having substantially equal angles of 120° between them. Projecting downwardly, with respect to the orientation of FIG. 4, from each arm 78 is a combination leg and tracing stylus member 80, having a rounded point 82. Members 80 may, for example, be attached to arms 78 by any of the methods described in connection with fixing threaded member 22 to triangular member 40. Central portion 76 is also provided with mounting means 84, comprising three unthreaded bores for use in mounting the upper cast.

Lower member 74 is substantially T-shaped, with the ends of each leg 86 corresponding in position to stylus members 80. At the end of each arm 86, directly below each stylus member 80 is a hollow or depression 88, into which a further charge of the acrylic molding material or the like 54 may be placed. In the central portion of member 74 is disposed another set of mounting means 90 similar to mounting means 84. The mounting means 84 and 90 correspond in position to mating mounting means 92 in each mounting plate 56. Mounting means 92 comprises one threaded bore and two index pins, the pins preferably having somewhat tapered tips. The upper and lower casts may therefore be easily attached to the upper and lower members of the articulator by one machine screw each or the like, inserted through one of the bores of mounting means 84, alignment being assured by the prior insertion of the indexing pins.

After the intra oral tracing has been accomplished, the molding material 52, with tracing apparatus attached thereto, is removed from the mouth and mounted onto the upper and lower casts. The upper and lower casts are then attached to the members of the articulator, by means of the mounting plates 56 embedded therein. Ideally, when the casts are so mounted, and the upper member of the articulator rests on the tracing assembly, the tracing table and tracing stylii of the articulator will be approximately 1 millimeter apart. This distance can be adjusted in the course of affixing the casts to the articulator, by methods known in the art.

After the casts have been mounted to the articulator, the upper member and upper cast are removed in order that more of the acrylic molding material may be placed into each of the depressions 88. The point 82 of each stylus is lubricated with silicone, and the upper member of the articulator is carefully placed back into position, with the stylii of the tracing apparatus resting within the original gothic arch traces. At this point, the tracing stylii are in intimate dynamic contact with the gothic arch traces. By holding both members of the articulator, with the aid of finger and thumb holds 92, and passing the original tracing through all of its excursions, the original gothic arch traces can be substantially identically reproduced on the articulator. The original, dynamic, patient derived articulation information is therefore substantially identically reproduced on the instrument which will be used to build a specific dentition for a particular patient. After the articulator has been moved through all of its excursions, the upper member thereof is removed in order that the acrylic molding material can harden or set. Once hardened, the tracing apparatus can be removed from the molds or casts, and artificial teeth can be inserted in the conventional fashion. It may be appreciated that even though the dentition is constructed in the conventional manner, when placement of teeth is tested by further excursions of the articulator, such excursions still represent the unique three dimensional envelope of motion generated for that particular patient. Placement of the teeth need not be tested against the predisposed "universal" movements of prior art articulators. As a further advantage, the manner in which the articulator may be prevented from moving within the defined envelope of motion determined by the gothic arch traces offers insightful information as to the orientation in which any particular teeth have been incorrectly placed, as well as what steps should be taken to correct the misplacement. Accordingly, even when the conventional placement of teeth within the dentition can proceed at a quicker pace.

Due to the fact that the articulator may be substantially contructed from inexpensive materials, such as metals, plastics, or even wood, the lower members, with gothic arch traces molded thereon, may be easily stored in case any future or further work must be done on the patient's dentition.

Taken together, the method and apparatus taught herein provide a novel and highly accurate system for obtaining a patient's "envelope of motion" during tooth contact and swallowing acts, and for transferring the "envelope of motion" to an articulator where it forms the basis for accurate and intelligent construction of full upper and lower dentures.

The present invention may be embodied in other specific forms without departing from the spirit or essential attributes thereof, and accordingly, reference should be made to the appended claims rather than to the foregoing specification as determining the scope of this invention.

I claim:

1. In the construction of dentures, a method for calibrating an articulator, said method comprising the steps of:

(a) rigidly and intra-orally mounting a tracing table member to one of a patient's upper and lower jaws;

(b) rigidly and intra-orally mounting a scribing member to the other of said patient's jaws;

(c) adjusting and locking the angular relationship and distance between bearing surfaces of said tracing table and said scribing member to bring said bearing surfaces into contact when said jaws are held slightly apart;

(d) forming a first set of three gothic arch traces, the traces defining a three-dimensional envelope of motion; and, (e) utilizing the first set of traces to form a substantially identical second set of gothic arch traces on the articulator, whereby relative movement of the articulator may be confined to the envelope of motion after the first set of gothic arch traces has been removed.

2. The method of claim 1, wherein the first set of gothic arch traces is patient generated by natural jaw movement while the angular relationship and distance between said bearing surfaces are locked in the adjusted position.

3. The method of claim 1, wherein an intra oral tracing apparatus is first inserted into a patient's mouth, and charged with a molding material, the first set of gothic arch traces being formed in the material in accordance with movement of the patient's jaw.

4. The method of claim 1, wherein the tracing apparatus is charged with the molding material prior to insertion into the patient's mouth.

5. The method of claim 1, wherein said adjustment is made by positioning and locking a universally-adjustable mechanism having a base member rigidly mounted to one of said jaws and a bearing surface unit universally-adjustable thereto.

6. The method of claim 5, wherein said universally-adjustable mechanism is a threaded, slit ball joint and said base member comprises at least one locking screw.

7. A method for constructing dentures, or the like, comprising the steps of:

(a) forming a first set of three gothic arch traces for movement of a patient's jaw, the gothic arch traces defining a three-dimensional envelope of relative jaw motion;

(b) utilizing the first set of traces to form a substantially identical second set of traces on an articulator having an upper denture holding member and a lower denture holding member to which members said dentures may be affixed, said upper holding member and lower holding member being placeable one upon the other but removable one from the other, whereby the interface of said dentures may be limited to said envelope of motion after removal of said first set of traces, but said dentures may be freely separated for further procedures; and, (c) placing teeth in the dentures in accordance with the defined movement of the articulator.

8. The method of claim 7, wherein the first set of gothic arch traces is formed intra orally.

9. The method of claim 7, wherein an intra oral tracing apparatus is first inserted into a patient's mouth, and charged with a molding material, the first set of gothic arch traces being formed in the material in accordance with movement of the patient's jaw.

10. The method of claim 9, wherein the tracing apparatus is charged with the molding material prior to insertion into the patient's mouth.

11. The method of claim 7, further comprising the step of testing placement of the teeth by moving the articulator through all excursions within the envelope of motion defined by the gothic arch traces.

12. The methods of claims 1 or 7, wherein the articulator comprises at least two unjoined members.

* * * * *